United States Patent [19]

Fohler

[11] Patent Number: 4,560,314
[45] Date of Patent: Dec. 24, 1985

[54] MAGAZINE ARRANGEMENT FOR MEASURING AND/OR SAMPLING PROBES

[75] Inventor: Johann Fohler, Puchenau, Austria

[73] Assignee: Voest-Alpine Aktiengesellschaft, Linz, Austria

[21] Appl. No.: 557,352

[22] Filed: Dec. 1, 1983

[30] Foreign Application Priority Data

Dec. 9, 1982 [AT] Austria ................. 4473/82

[51] Int. Cl.$^4$ .................. C21C 5/30; B65G 1/08
[52] U.S. Cl. .................. 414/276; 414/745; 414/748
[58] Field of Search ........... 414/276, 748, 189, 199, 414/207, 745; 193/33, 34; 232/49, 51

[56] References Cited

U.S. PATENT DOCUMENTS 3,700,116 10/1972 Rysti ................. 414/748
3,753,507 8/1973 James et al. ......... 414/276

FOREIGN PATENT DOCUMENTS 2315061 10/1973 Fed. Rep. of Germany .
2839255 3/1980 Fed. Rep. of Germany .
3044609 6/1982 Fed. Rep. of Germany .

Primary Examiner—Robert G. Sheridan
Attorney, Agent, or Firm—Brumbaugh, Graves, Donohue & Raymond

[57] ABSTRACT

A magazine for measuring and/or sampling probes includes storage compartments accommodating the probes in a horizontal position, and supply and delivery openings provided parallel to the probes. A conveying means is arranged at the delivery openings to deliver the probes to an erecting means placing the probes in a vertical position. In order to ensure an optimum utilization of space with little space being required beside the magazine, the magazine comprises a plurality of superposed storage compartments provided with a roll bevel for the probes. Their vertically superposed delivery openings are passed by a lift for accommodating one probe each from one of the storage compartments. The lift is movable to the erecting means from a delivery opening each.

5 Claims, 6 Drawing Figures

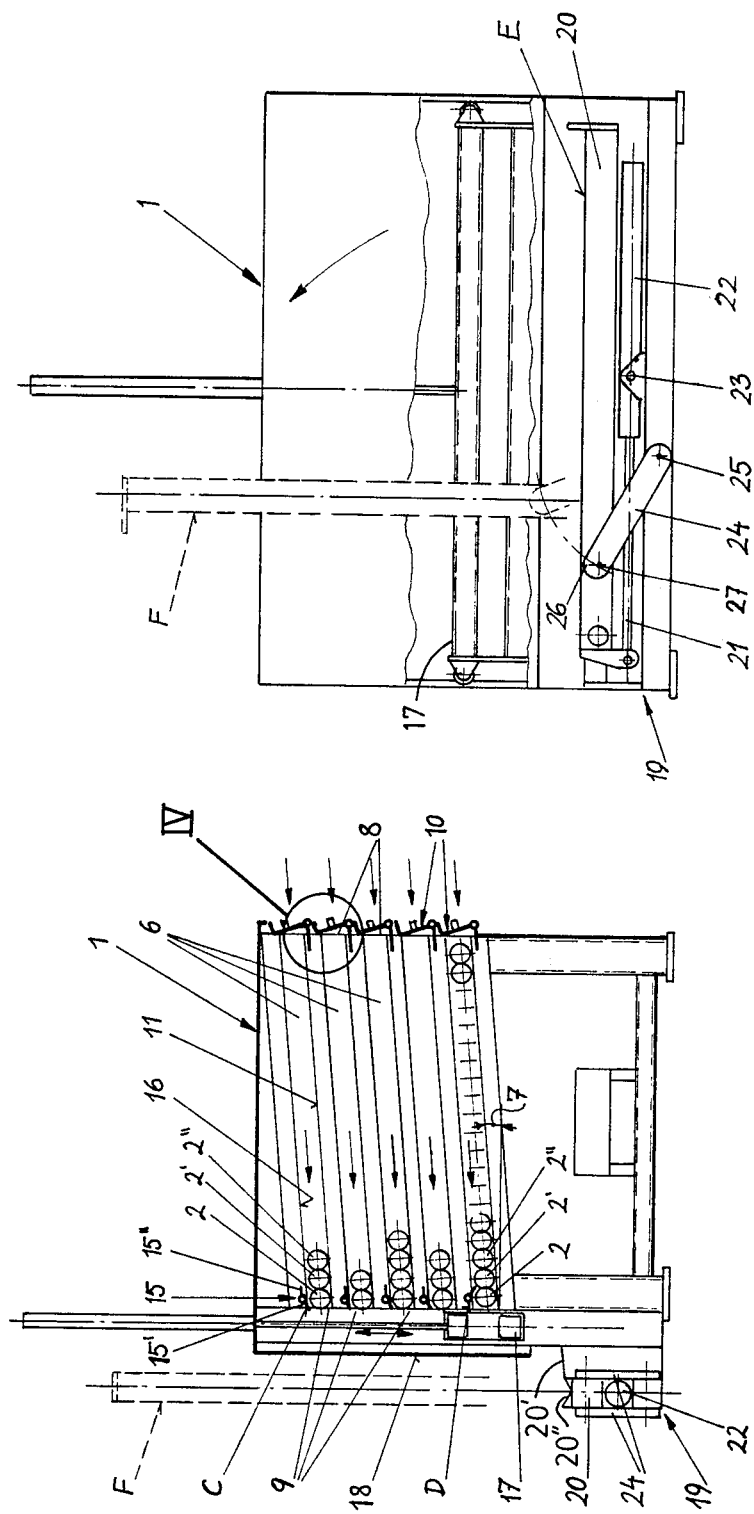

MAGAZINE ARRANGEMENT FOR MEASURING AND/OR SAMPLING PROBES

BACKGROUND OF THE INVENTION

The invention relates to a magazine for measuring and/or sampling probes, in particular for steel works, comprising storage compartments accommodating the probes in a horizontal position, and supply and delivery openings provided parallel to the probes, with a conveying means located at the delivery openings to deliver the probes to an erecting means which places the probes in a vertical position.

A magazine of this kind is known from DE-A No. 30 44 609. This known magazine comprises vertically extending storage compartments which, due to the probes' own weight, can be filled with a limited number of probes. Difficulties with this magazine arise with the filling of the magazine and the withdrawal of the probes. If the magazines are filled in a direction transverse to the longitudinal direction of the probes, it is difficult to fill the storage compartments lying between other storage compartments; if the storage compartments are filled in the axial direction of the probes (known from DE-B No. 28 39 255), a free space at least the length of the probes is required laterally adjacent to the magazine. If the probes are removed by pushing them out of the compartments in the longitudinal direction of the probes, additional space is required on the side of the magazine opposite the filling side, which space also must have a width corresponding to the lengths of the probes.

When conveying the probes out of the vertical compartments, the remaining probes in a compartment may become damaged by falling a distance corresponding to the diameter of a probe.

It is impracticable to extract in their longitudinal direction if probes having offset diameters, e.g., probes comprising special measuring heads, are used. If the probes are taken out transversely to their longitudinal extension, as is disclosed in DE-A No. 30 44 609, a singling means carrying the remaining probes present in the respective storage compartments is necessary.

The present invention avoids these disadvantages and difficulties and has as its object to provide a magazine of the initially defined kind, in which as many probes as possible can be housed by optimum space utilization, in which the supply and delivery of the probes requires a small space beside the magazine, and with which the probes are carefully delivered. In particular, the invention allows for installation of the magazine in an existing steel works with narrow limited available space.

SUMMARY OF THE INVENTION

According to the present invention, this object is achieved by providing a magazine comprising a plurality of superposed storage compartments having a roll bevel for the probes and whose vertically superposed delivery openings are passed by a lift for accommodating one probe each from one of the storage compartments, the lift being movable to the erecting means from the delivery openings.

In order to easily introduce the probes into the magazine, the storage compartments suitably are closeable at the supply openings by means of angularly shaped flaps, which are each mounted on the magazine so as to pivot about the angle-forming edge at the bottom of each storage compartment.

For a particularly gentle delivery of the probes, the storage compartments, at the delivery openings, advantageously are each provided with a retention flap pivotably mounted at the ceiling of each storage compartment.

Suitably, the retention flap is mounted above the probe that lies next to the delivery opening and includes two projections disposed at an obtuse angle to each other. A first of the projections is directed towards the delivery opening and the second projection is directed towards the probe that is next to the foremost probe, the flap being pivotable from a position in which the first projection is in contact with the foremost probe into a position in which the second projection is in contact with the probe mext to the foremost probe, upon release of the foremost probe.

In order to erect the probes in a particularly small space, the erecting means, according to a preferred embodiment, comprises a rocker pivotably mounted on the magazine and hinged, with its freely pivotable end, to a probe holder taking over a probe from the lift.

BRIEF DESCRIPTION OF THE DRAWINGS

The invention will now be explained in more detail by way of one embodiment and with reference to the accompanying drawings, wherein:

FIGS. 2 and 3 are partially sectioned side views according to the arrows II and III of FIG. 1;

DESCRIPTION OF THE PREFERRED EMBODIMENT

Figure 1:
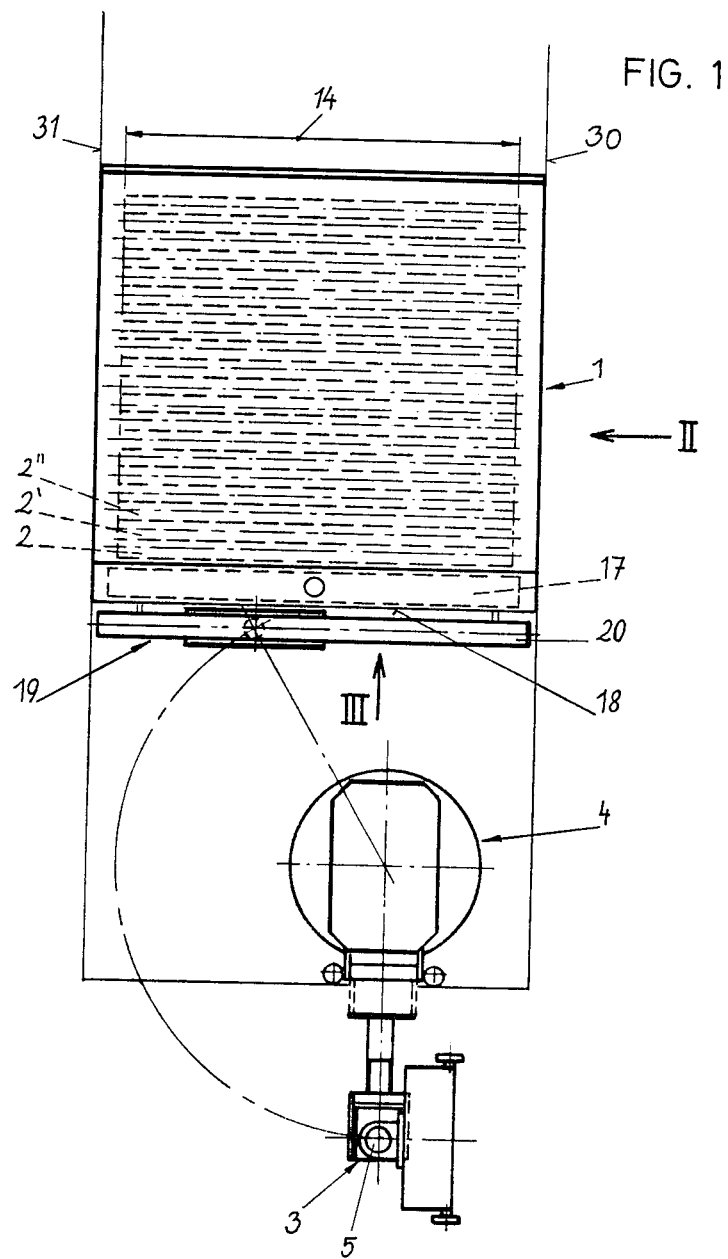
FIG. 1 is a top view of a magazine established in a steel works.

A magazine 1 to accommodates measuring and/or sampling probes 2, 2', 2'', . . . , which are used to make measurements in, or samplings from, a steel works converter by withdrawing a probe from the magazine 1 by means of grip pliers 3 of a manipulator 4 and slipping it on to the lower end of a lance 5 that may be introduced vertically into the converter.

As is apparent, in particular, from FIGS. 2 and 3, the magazine 1 comprises vertically superposed storage compartments 6 to accommodate the probes 2, 2', 2'', . . . , a plurality of probes being mounted in each storage compartment 6. The storage compartments 6 are arranged so as to be inclined slightly at an angle 7 so that the probes inserted in the supply opening 8 of each storage compartment 6 automatically roll to the delivery opening 9 on the other end of the storage compartments 6. The vertically superposed supply openings 8 are closeable by means of flaps 10 of angular cross sectional shape, each flap being mounted so as to be pivotable at the height of the bottom 11 of each storage compartment 6 about a pivot axis 12 provided parallel to the longitudinal direction of the supply opening 8. The pivot axis is provided on the angle-forming edge 13 of the angular flap 10.

Figure 5:
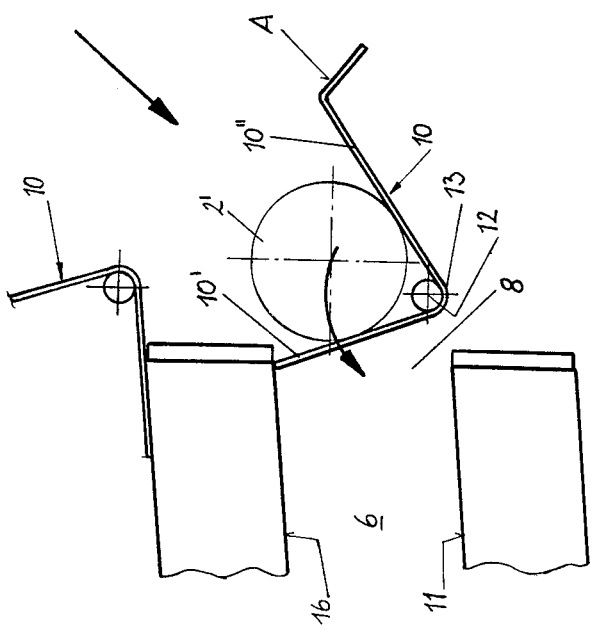
FIGS. 4 and 5 show in detail the area labeled as IV in FIG. 2 on an enlarged scale.
Figure 4:
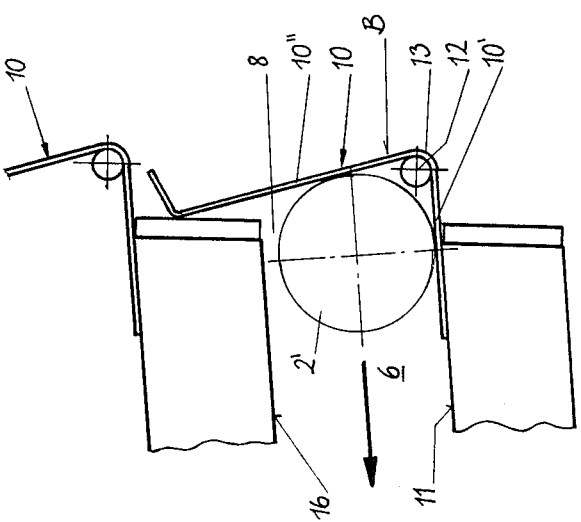

As can be seen from FIGS. 4 and 5, a probe 2' is each placed between the angularly arranged flap parts 10', 10'', with the flap 10 pivoted into the supply position A, and the flap 10 is then pivoted into the closed position B with the probe 2' rolling from the flap 10 into the storage compartment 6. Since the pivot axis 12 of each flap 10 is arranged parallel to the supply openings 8 which have a length that corresponds to the length 14 of the probes 2, 2', 2", . . . , the probes, within the storage compartments 6, roll as far as to the delivery openings 9, or as far as to the probe already supplied to behind the delivery openings, without canting.

At the delivery openings 9, a singling means 15 is provided per storage compartment 6, which is designed as a retention flap 15. Each retention flap 15 is pivotably movably mounted on the ceiling 16 of the storage compartment above the probe 2 lying next to the delivery opening and comprises two projections 15', 15" located at an obtuse angle to each other. A first projection 15' is directed towards the delivery opening 9 and can be brought into contact with the first probe 2, lying by the delivery opening 9, with the retention flap 15 being in the closed position C. The second projection 15", which is directed towards the probes 2', 2", . . . neighboring the first probe 2, in the released position D of the retention flap 15, contacts the probe 2' neighboring the first probe 2 and thus retains the same and the probes 2", . . . arranged therebehind in the respective storage compartment 6 so that only the first probe 2 will roll out of the storage compartment (cf. the lowermost storage compartment 6 in FIG. 2).

The probes 2 rolling out of the storage compartments 6 are taken up by a lift 17 movable in the vertical direction and passing all the delivery openings 9 that are superposed in the vertical direction. By means of the lift 17 each probe 2 is individually conveyed alongside an erecting means 19 arranged on the front side 18 of the magazine 1. Probe 2 rolls from lift 17 down incline 20' into notch °''' on a probe holder 20. The erecting means 19 comprises the probe holder 20 which is pivotable from a horizontal position E into a vertical position F. For this purpose, the probe holder 20, on one end, is connected with the piston rod 21 of a pressure medium cylinder 22, which, in turn, is pivotable about a pivot axis 23 provided on the magazine 1.

The probe holder 20 is mounted by two parallel rockers 24, which are mounted each with one end on the magazine 1 so as to be pivotable about a pivot axis 25. Each of the other freely pivotable ends 26 are articulately fastened to the probe holder 20.

Figure 6:
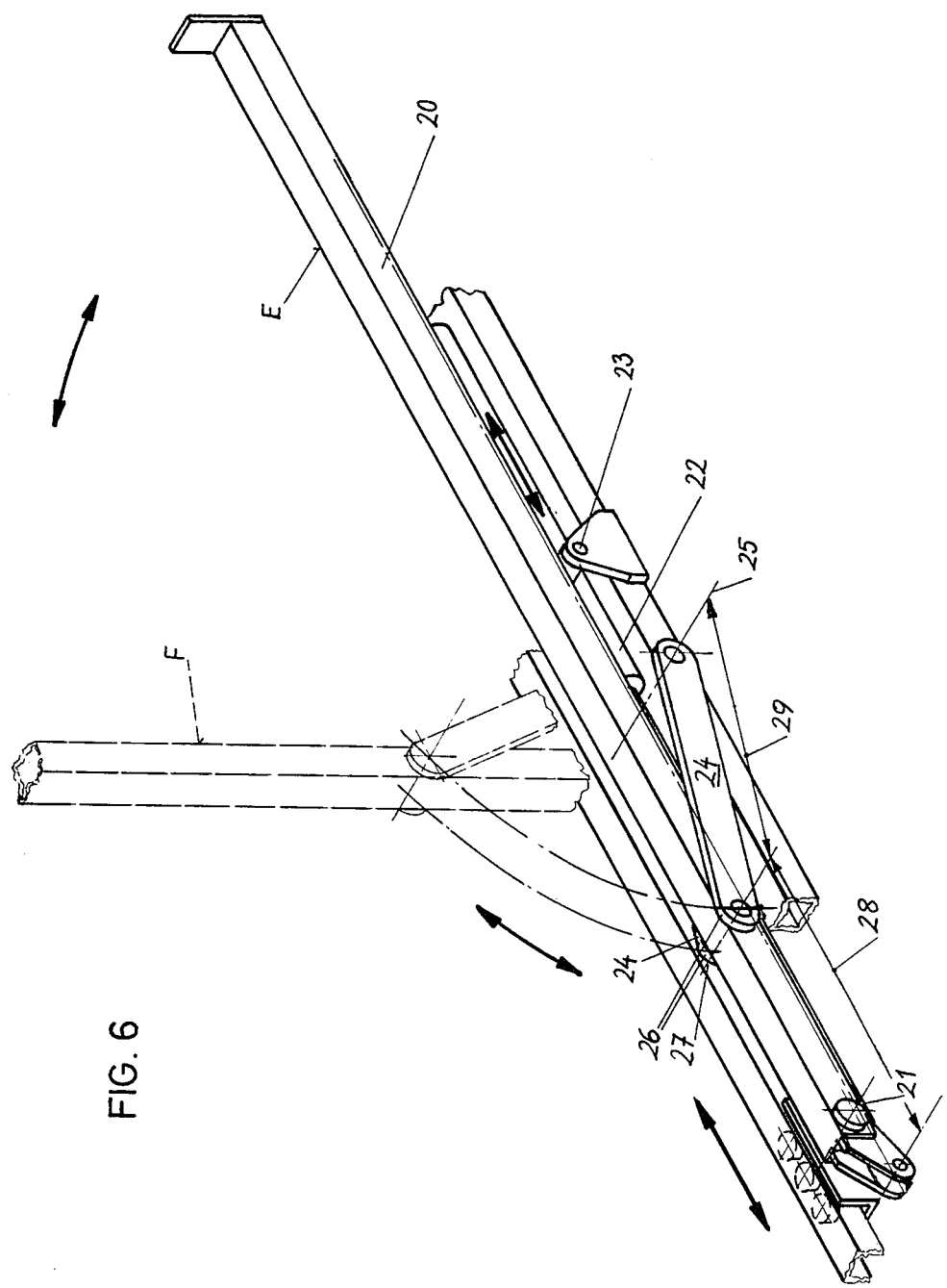
FIG. 6 illustrates a detail of the erecting means in an isometric view.

The articulation axis 27 connecting the freely pivotable ends 26 of the rockers 24 with the probe holder is provided between the ends of the probe holder, i.e., at a distance 28 from the hinging point of the pressure medium cylinder piston 21 that corresponds approximately to the length 29 of the rocker. As is apparent from FIG. 6, the probe holder is thereby pivotable into an upright vertical position F without any space being required laterally beside the magazine 1 or below the magazine.

From FIG. 1 it can be seen that no space is required laterally beside the limitation lines 30, 31 of the magazine 1 entered in FIG. 1, i.e., neither to fill the magazine nor to take out a probe, so that the magazine according to the invention may be planned into already existing steel works by saving as much space as possible.

What I claim is:

1. In a magazine for measuring and/or sampling probes for use in a steel works or the like, of the type including compartments for storing said probes in a horizontal position, supply and delivery openings arranged parallel to said probes, conveying means arranged at said delivery openings, and erecting means adapted to place said probes into a vertical position when said probes are delivered to said erecting means by said conveying means, the improvement comprising a plurality of superposed storage compartments constituting a magazine, said superposed storage compartments having vertically superposed delivery openings at one end of said magazine, said storage compartments being inclined to allow said probes to roll from said supply openings towards said delivery openings, and a lift passing by said vertically superposed delivery openings and adapted to receive one of said plurality of probes from any one of said plurality of storage compartments, said lift being movable from one of said delivery openings to said erecting means to convey a probe thereto.

2. An arrangement as set forth in claim 1, further comprising angularly shaped flaps to close said storage compartments at said supply openings, and wherein each of said storage compartments has a bottom and each of said angularly shaped flaps has an angle-forming edge and is mounted on said magazine at the height of said bottom so as to be pivotable about said angle-forming edge.

3. An arrangement as set forth in claim 1, wherein each of said storage compartments has a ceiling and a retention flap is provided for each of said storage compartments at the pertaining delivery opening mounted in a manner so as to be pivotable at the height of said ceiling.

4. An arrangement as set forth in claim 3, wherein said retention flap is mounted above the one of said probes lying next to said delivery opening and comprises a first projection directed towards said delivery opening and a second projection arranged at an obtuse angle to said first projection and directed towards the one of said probes neighboring the foremost of said probes, said retention flap being pivotable from a position in contact with the foremost of said probes by said first projection into a position in contact with the one of said probes neighboring the foremost of said probes by said second projection upon release of the foremost of said probes.

5. An arrangement as set forth in claim 1, 2, 3 or 4, further comprising a probe holder adapted to take over one of said probes from said lift, and a rocker mounted in said erecting means so as to be pivotable on said magazine and hinged to said probe holder with its freely pivotable end.

* * * * *